US008834796B2

(12) United States Patent
Jarrell

(10) Patent No.: US 8,834,796 B2
(45) Date of Patent: Sep. 16, 2014

(54) CHROMATOGRAPHIC OPTICAL DETECTION SYSTEM

(71) Applicant: Waters Technologies Corporation, Milford, MA (US)

(72) Inventor: Joseph A. Jarrell, Newton Highlands, MA (US)

(73) Assignee: Waters Technologies Corporation, Milford, MA (US)

(*) Notice: Subject to any disclaimer, the term of this patent is extended or adjusted under 35 U.S.C. 154(b) by 0 days.

(21) Appl. No.: 13/857,552

(22) Filed: Apr. 5, 2013

(65) Prior Publication Data

US 2013/0269424 A1 Oct. 17, 2013

Related U.S. Application Data

(60) Provisional application No. 61/623,635, filed on Apr. 13, 2012.

(51) Int. Cl.
*G01N 21/00* (2006.01)
*G01N 15/10* (2006.01)
*G01N 15/14* (2006.01)
*G01N 30/00* (2006.01)
*G01N 15/06* (2006.01)
*G01N 30/74* (2006.01)
*G01N 35/00* (2006.01)
*G01N 33/48* (2006.01)
*G01N 30/84* (2006.01)

(52) U.S. Cl.
CPC ............ *G01N 15/1429* (2013.01); *G01N 30/00* (2013.01); *G01N 15/065* (2013.01); *G01N 30/74* (2013.01); *G01N 2030/8447* (2013.01)
USPC .................. 422/82.05; 422/82.06; 422/82.07; 422/82.08; 356/335; 356/336; 356/337; 356/338; 435/40.51; 436/43; 436/50; 436/52; 436/164

(58) Field of Classification Search
None
See application file for complete search history.

(56) References Cited

U.S. PATENT DOCUMENTS

2008/0319680 A1* 12/2008 Fox et al. ........................ 702/21

OTHER PUBLICATIONS

Allen, Lori B. et al: Condensation Nucleation Light Scattering: A New Approach to Development of High-Sensitivity, Universal Detectors for Separations, Anal. Chem. 1993, 65, 841-844.
Stolzenburg, Mark R. et al: An Ultrafine Aerosol Condensation Nucleus Counter, Aerosol Science and Technology 14:48-65 (1991).

* cited by examiner

*Primary Examiner* — Neil N Turk
(74) *Attorney, Agent, or Firm* — Water Technologies Corporation

(57) ABSTRACT

A chromatographic optical detection system includes an optical detector disposed to receive light scattered from a stream of particles and configured to convert the received light to an electrical signal; a signal-processing unit in signal communication with the optical detector to receive the electrical signal, and configured to convert the electrical signal to digital pulses and count the digital pulses to output a first signal corresponding to a number of particles detected in a time interval, and configured to integrate and digitize the electrical signal to output a second signal corresponding to the number of particles detected in the time interval; and a data station in signal communication with the signal-processing unit, and configured to select the first signal, if the number of particles detected in the time interval is less than a threshold criterion, and to select the second signal if the number of particles detected in the time interval exceeds the threshold criterion. The threshold criterion is associated with a saturation condition.

15 Claims, 6 Drawing Sheets

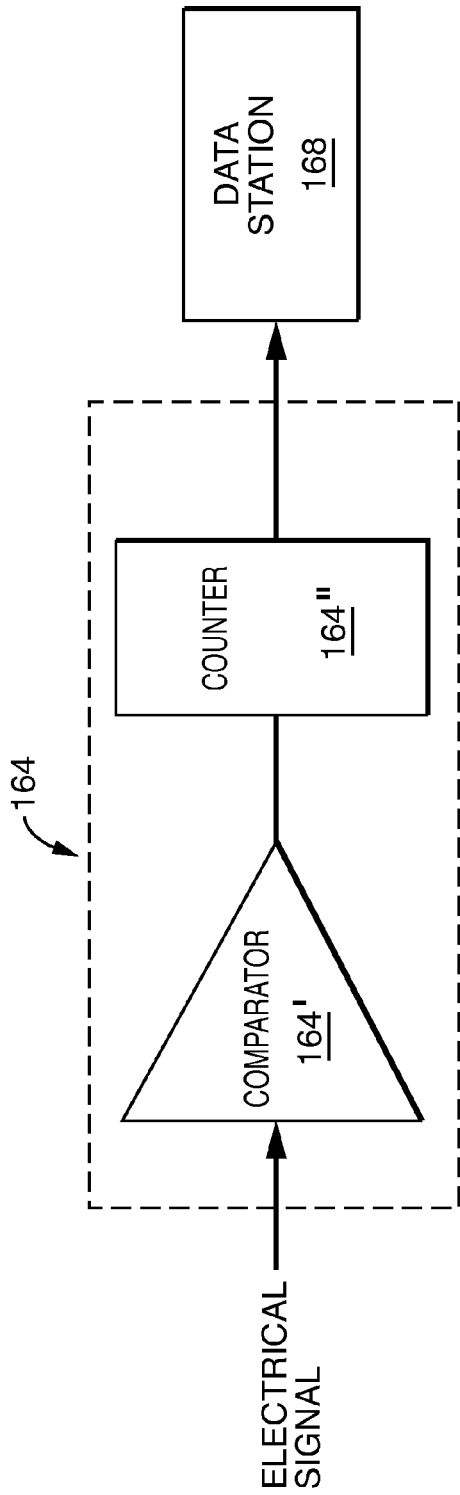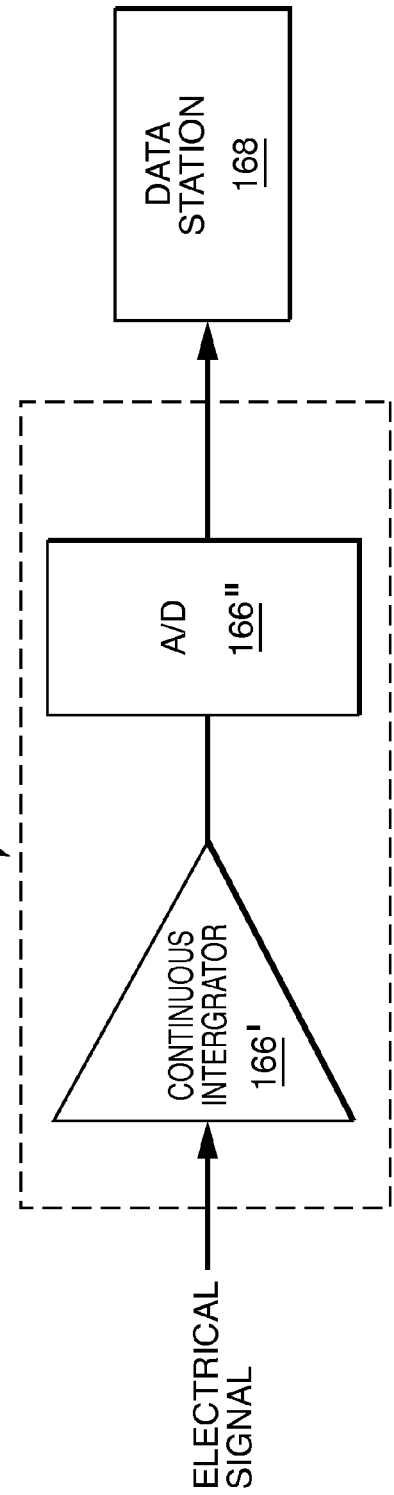

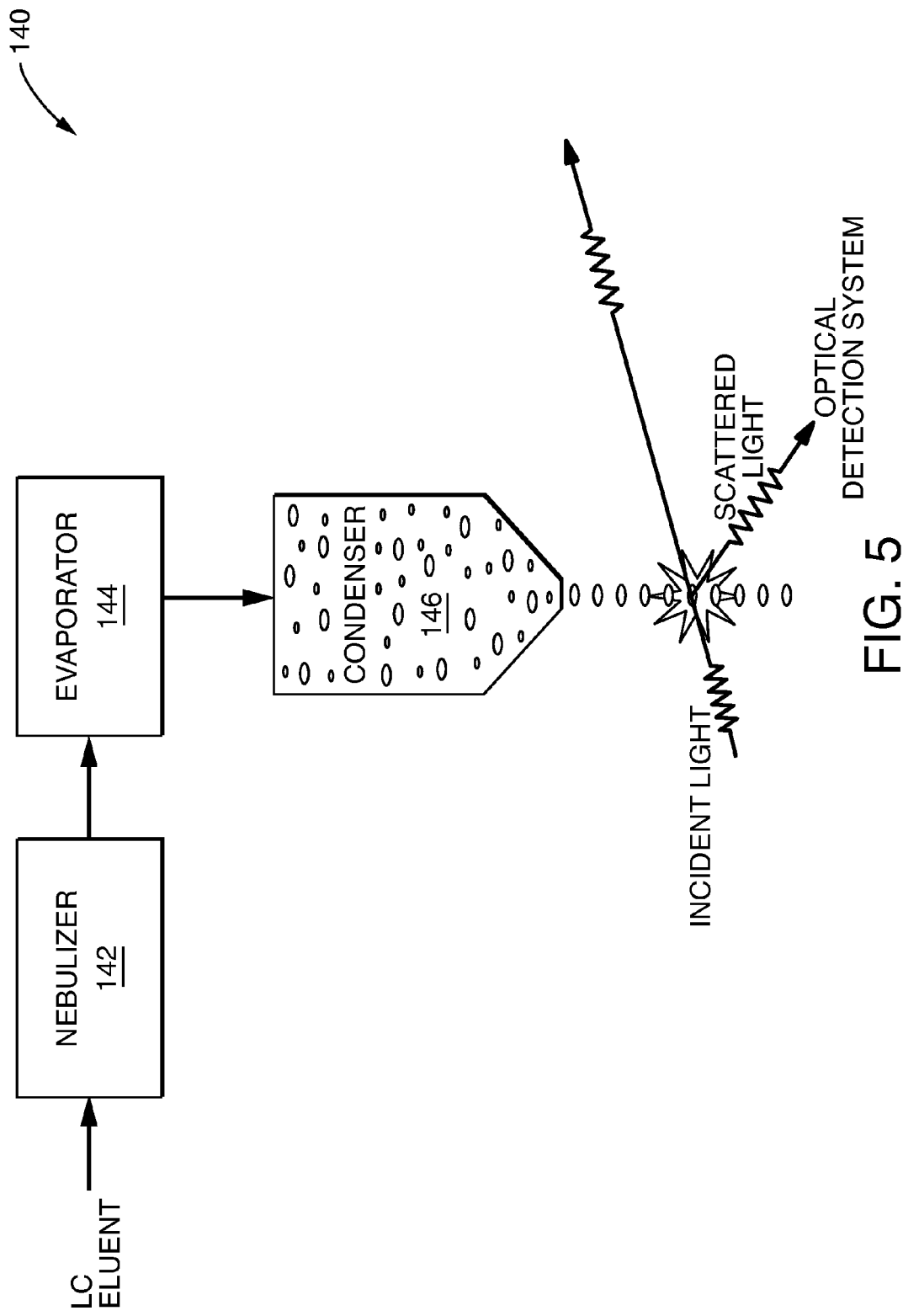

CHROMATOGRAPHIC OPTICAL DETECTION SYSTEM

CROSS REFERENCE TO RELATED APPLICATIONS

This application claims priority from and the benefit of U.S. Provisional Application No. 61/623,635, filed on Apr. 13, 2012. The entire contents of the application are incorporated herein by reference.

BACKGROUND

Condensation nucleation light scattering detection (CNLSD), when combined with nebulization, is a technique for detection of analytes separated by liquid chromatography (LC). A LC eluent carrying separated analytes is nebulized, dried and delivered to a CNLSD device. There, a stream of analyte particles is detected by scattering light from the particles after they are enlarged by condensation. CNLSD is considered to be universal for its ability to detect any analytes that are less volatile than the mobile phase carrying the analytes. Unfortunately, some light detectors do not provide adequate sensitivity and linear response over a wide dynamic range.

SUMMARY

Some embodiments arise, in part, from the realization that a chromatographic optical detection system can advantageously be configured to have linear responsiveness and high sensitivity over a wide dynamic range by incorporating two signal processing modes: a pulse-counting mode and an analog integration mode. Such embodiments extend response linearity to high level signals while retaining good sensitivity for weak signals.

One embodiment features a chromatographic optical detection system that includes: an optical detector disposed to receive light scattered from a stream of particles and configured to convert the received light to an electrical signal; a signal-processing unit in signal communication with the optical detector to receive the electrical signal, and configured to convert the electrical signal to digital pulses and count the digital pulses to output a first signal corresponding to a number of particles detected in a time interval, and configured to integrate and digitize the electrical signal to output a second signal corresponding to the number of particles detected in the time interval; and a data station in signal communication with the signal-processing unit, and configured to select the first signal, if the number of particles detected in the time interval is less than a threshold criterion, and to select the second signal if the number of particles detected in the time interval exceeds the threshold criterion. The threshold criterion is associated with a saturation condition.

Another embodiment provides a method of optical detection in a chromatography system that includes: detecting light scattered from a stream of particles; converting the detected light to an electrical signal; converting the electrical signal to digital pulses, at least if a rate associated with the stream of particles is less than a saturation condition; integrating the electrical signal, at least if the rate of the stream of particles exceeds the saturation condition; determining a number of particles detected in a time interval from the digital pulses, if the number of particles detected in the time interval is less than a threshold criterion; and determining the number of particles detected in the time interval from the integrated signal, if the number of particles detected in the time interval exceeds the threshold criterion. The threshold criterion is associated with the saturation condition.

In some implementations, the signal-processing unit includes a first signal processor and a second signal processor. The first signal processor is configured to convert the electrical signal to the digital pulses and count the digital pulses to output a first signal, and the second signal processor is configured to integrate and digitize the electrical signal to output a second signal. The saturation condition is associated with saturation of the first signal processor.

In some cases, the electrical signal is composed of a series of amplified voltage pulses produced from the optical detector.

In some implementations, the threshold criterion is a predetermined frequency of the amplified voltage pulses, above which the first signal processor is known to saturate.

In other implementations, the threshold criterion is a frequency of the amplified voltage pulses, above which the converted digital pulses overlap.

In some cases, the data station selects the first signal if the frequencies of the amplified voltage pulses are below the threshold criterion and selects the second signal if the frequencies exceed the threshold criterion.

In some implementations, the optical detector includes an optical sensor and an amplifier. In some implementations, the optical detector includes a photo-diode, a photo-diode array, or a photomultiplier tube. In some cases, the first signal processor includes a comparator and a digital counter, and the second signal processor includes a continuous integrator and an analog-to-digital convertor.

In certain implementations, the system further includes: a liquid chromatography system eluting a mobile phase carrying one or more analytes separated by the liquid chromatography system; a nebulizer configured to spray the liquid chromatography eluent into a mist of droplets; an evaporator configured to evaporate the mobile phase from the mist of droplets to produce a stream of particles associated with the one or more analytes; a condenser including a supersaturated vapor, which condenses upon the particles to grow the particles to a larger size; and at least one light source generating at least one beam of light that strikes the enlarged particles and is scattered by the enlarged particles. The light scattered by the enlarged particles is received by the optical detector and converted to the electrical signal.

In certain implementations, the method further includes: forming the stream of particles including: generating a liquid chromatography eluent including a mobile phase carrying one or more analytes separated by liquid chromatography; nebulizing the liquid chromatography eluent into a mist of droplets; evaporating the mobile phase from the mist of droplets to produce a stream of particles associated with the one or more analytes; and condensing a supersaturated vapor upon the particles to grow the particles to a larger size. The enlarged particles pass through at least one beam of light to scatter the light.

Other aspects, features, and advantages are in the description, drawings, and claims.

BRIEF DESCRIPTION OF THE DRAWINGS

In the drawings, same or like reference characters and numbers generally refer to same or like elements throughout different views. Also, the drawings are not necessarily to scale.

FIG. 4A is a schematic view of one embodiment of the first signal processor and the data station of FIG. 3.

FIG. 4B is a schematic view of one embodiment of the second signal processor and the data station of FIG. 1.

FIG. 5 is a schematic view of the particle-forming system of FIG. 1.

DETAILED DESCRIPTION

Some illustrative implementations will now be described with respect to FIGS. 1-6. In view of this description, modifications and alterations to these implementations will be apparent to one of ordinary skill.

Figure 1:
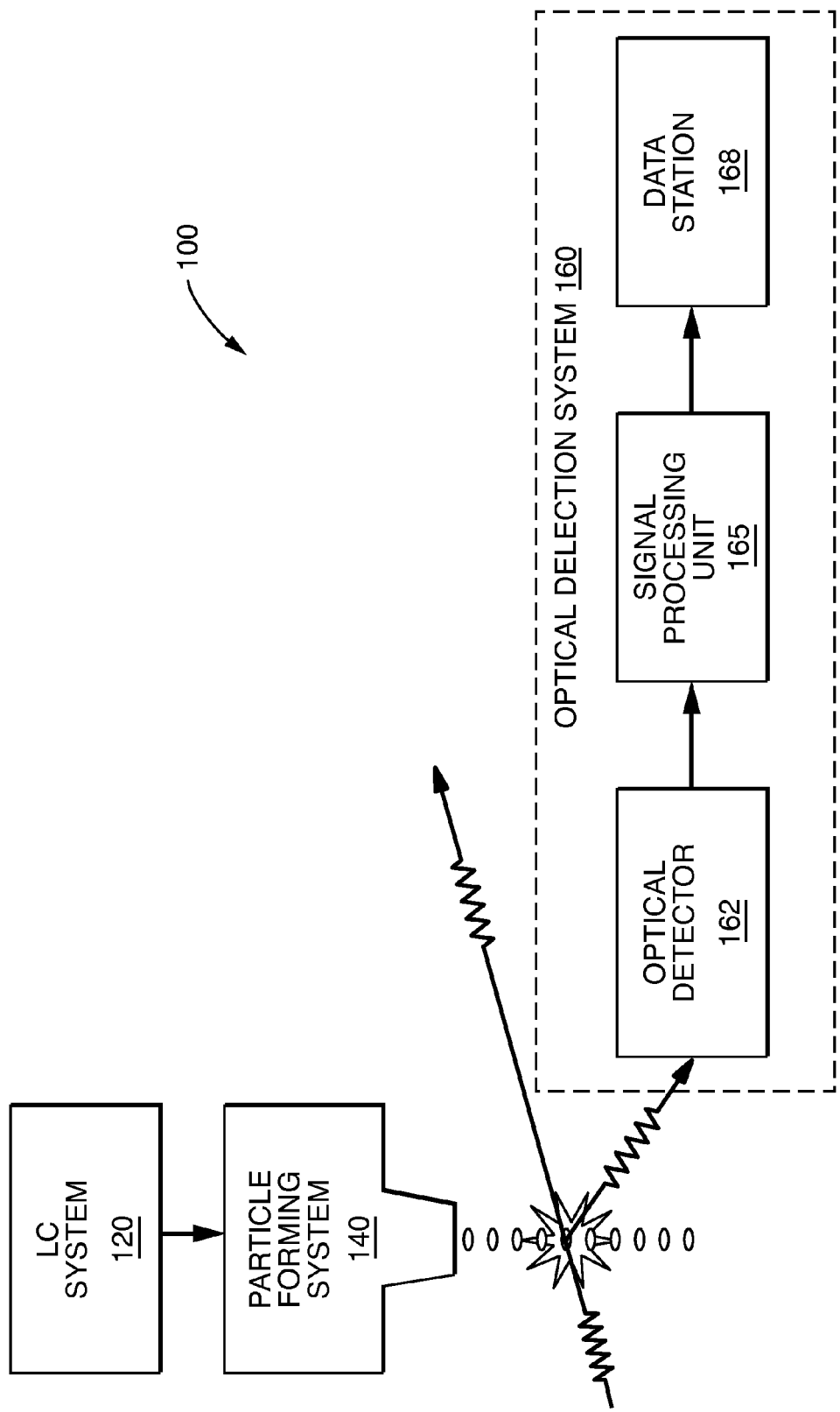
FIG. 1 is a schematic overview of a chromatographic optical detection system, including a LC system, a particle-form
Figure 2:
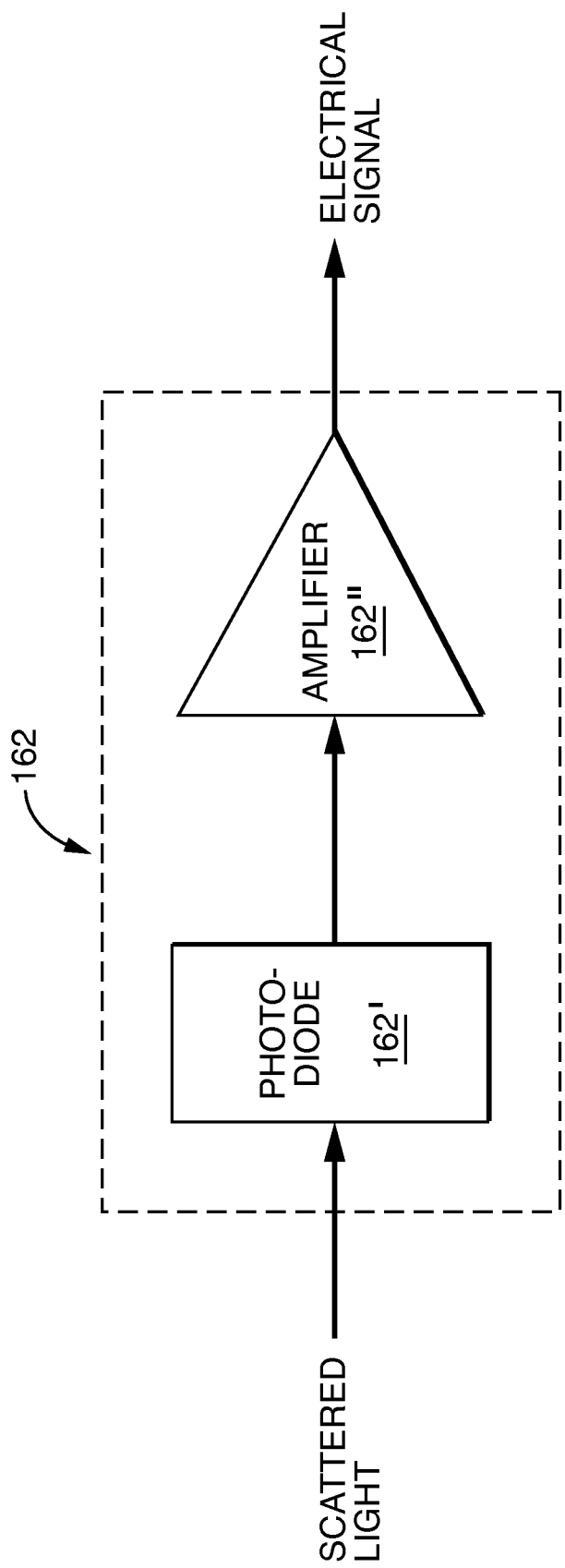
- FIG. 2 is a schematic view of one embodiment of the optical detector of FIG. 1.

Referring to FIG. 1, a chromatographic optical detection system 100 includes a LC system 120, a particle-forming system 140 and an optical detection system 160 that includes an optical detector 162, a signal-processing unit 165 and a data station 168.

The LC system 120 performs chromatography on a sample, mainly separating one or more analytes, contained in a sample, from one another. The separation can be carried out in an analytical column packed with a stationary phase. A sample containing analytes is introduced to a mobile phase and carried by the mobile phase through an analytical column, where dissimilar analytes elute from the column at different times due to their different affinities for the mobile phase and stationary phase. The mobile phase carrying the separated analytes elutes from the LC system 120 and flows to the particle-forming system 140.

The particle-forming system 140 transforms the LC eluent into a stream of analyte particles of optically effective size. The particle-forming system 140 nebulizes the LC eluent to form a mist of droplets and then evaporates the mobile phase to produce a stream of less volatile aerosol particles, associated with the analytes present in the LC eluent. Upon completion of the evaporation, the system 140 condenses a supersaturated vapor onto the aerosol particles to grow the particles from as small as a few nanometers up to about tens of micrometers in size. The enlarged particles travel through at least one incident light beam and scatter the light onto the optical detection system 160.

The optical detection system 160 includes the optical detector 162, the signal-processing unit 165 and the data station 168. The optical detector 162 is disposed to receive the light scattered by the particles and configured to convert the scattered light to an electrical signal, which, in some implementations, is composed of a series of amplified voltage pulses. The amplified voltage pulses are then directed to the signal-processing unit 165 for further processing.

The signal-processing unit 165 is configured to convert the amplified voltage pulses to digital pulses to form a first signal, corresponding to a number of particles detected in a time interval, and to integrate and digitize the amplified voltage pulses to form a second signal, corresponding to the number of particles detected in the time interval. The first and second signals are outputted to the data station 168.

The data station 168 is configured to receive both the first and second signals and select either one of them to form a data point of a detector's response profile. The data station 168 selects the first signal, if the number of particles detected in the time interval is less than a threshold criterion, and selects the second signal, if the number of particles detected in the time interval exceeds the threshold criterion. The threshold criterion is associated with a saturation condition, e.g., a frequency of the amplified voltage pulses, above which the converted digital pulses overlap.

In some implementations, the signal-processing unit 165 can include a high-speed analog-to-digital converter (not shown) which converts the electrical signal outputted by the optical detector 162 to digital pulses. For many CNLSDs, the width of these pulses is of the order of 500 nanoseconds. If a high-speed analog-to-digital converter is chosen such that it has a sampling rate of about 0.1 GHz or greater, then the digital output (i.e., the first signal) it produces will have sufficient resolution that the data station 168 can use as a primary source to form data points in a detector's response profile. When the digital pulses start overlapping (which can happen even with a very high-speed analog-to-digital converter), the data station 168 can then select the digitized integrated signal (i.e., the second signal) to form data points in the detector's response profile.

The optical detector 162 (shown in FIG. 2) includes an optical sensor 162' and an amplifier 162". The optical sensor 162' is disposed to receive the light scattered by the particles, produced from the particle-forming system 140, and configured to convert the scattered light into electrical current. The optical sensor 162' can be a photodiode, a photodiode array, or a photomultiplier tube (PMT). The electrical current produced from the optical sensor 162', typically on the order of magnitude of nano-amperes, is often too small to cross the noise cut-off threshold or reference level of the processor 164 and needs to be amplified by the amplifier 162", which is normally a current-to-voltage converter. The amplifier 162" can turn the electrical current into a series of amplified voltage pulses, which are then fed to the signal-processing unit 165.

Figure 3:
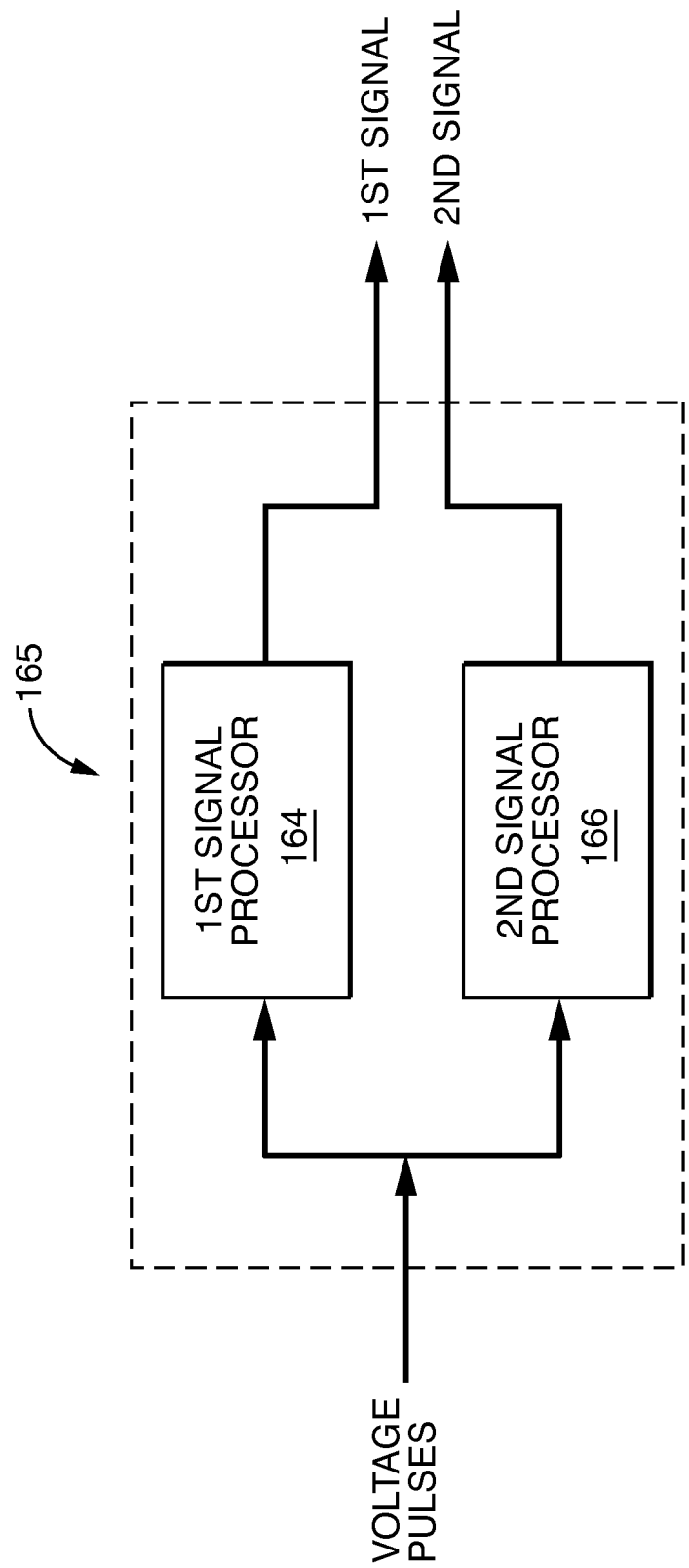
FIG. 3 is a schematic view of one embodiment of the signal-processing unit of FIG. 1.

FIG. 3 illustrates one embodiment of the signal-processing unit 165 of FIG. 1, which includes a first signal processor 164 and a second signal processor 166, parallel to each other. In this configuration, the amplified voltage pulses produced by the optical detector 162 are directed simultaneously to both the first and second signal processors 164 and 166.

The first signal processor 164 receives the voltage pulses and converts each of the voltage pulses to a digital pulse. The first signal processor 164 then counts the number of digital pulses generated in a given time interval to form a first signal, which corresponds to the number of particles detected in the time interval, and outputs the first signal to the data station 168.

The second signal processor 166 receives the voltage pulses, integrates the amplitudes of the voltage pulses generated in a given moving time interval, and periodically digitizes the integrated voltage pulses to form a second signal, which corresponds to the number of particles detected in the time interval between digital conversions, and outputs the second signal to the data station 168.

The data station 168 is configured to receive the outputs from both the first and second signal processors 164 and 166 and select one of the outputs to use at a time in formation of a detector response profile for the analytes, based on a threshold criterion. The threshold criterion is associated with saturation of the first signal processor 164. In some implementations, the threshold criterion is a predetermined frequency of the voltage pulses, produced from the optical detector 162, above which the first signal processor 164 is known to saturate. In some implementations, the threshold criterion can be a range of the frequencies, produced from the optical detector 162, near any of which the first signal processor 164 is known or likely to saturate. The data station 168 has a built-in intelligence, which, in some cases, monitors frequencies of the voltage pulses, as a chromatographic peak associated with one or more analytes passes through the system 100; compares the frequencies with the threshold criterion; and decides which output or signal to use based on the threshold criterion.

As used herein, the term "intelligence," in the broadest sense, refers to any means that gives the data station 168 the capabilities to decide which signal, the first signal or the second signal, to use in formation of a detector response profile, based on a threshold criterion. By way of example, without limitation, the intelligence can be one or more computer executable instructions, such as software or firmware modules, executed by one or more computers, or one or more hardware components with some logic circuits built-in.

In some implementations, the data station 168 selects the output of the first signal processor 164 if the frequencies are below the threshold criterion and selects the output of the second signal processor 166 if the frequencies exceed the threshold criterion. The data station 168 with the built-in intelligence permits the overall detector response to transition seamlessly between the outputs of the two processors 164 and 166.

As shown in FIG. 4A, the first signal processor 164, running in a pulse-counting mode, includes a comparator 164' and a counter 164". The comparator 164' receives the voltage pulses and triggers the counter 164" to either count or reset, based on the level of the incoming voltage pulses. When the rising edge of an incoming voltage pulse crosses the reference level of the comparator 164', the comparator 164' output level goes high, which causes the counter 164" to count. When the falling edge of an incoming voltage pulse drops below the reference level, the comparator 164" output goes low, which triggers the counter 164" to reset. Each cycle of the comparator 164" output, going from low to high, increments the counter 164" by one count, or in other words, is registered as one digital pulse by the counter 164". The time interval between when the counter 164" starts to count and when the counter 164" resets is a counting cycle of the signal processor 164. Ideally, only one voltage pulse is received by the comparator 164' during each counting cycle and the counter 164" resets after each voltage pulse is converted to a digit pulse.

The counter 164" counts digital pulses generated in a time interval, e.g., a second, to form an output signal which is sent to the data station 168. The number of the digital pulses generated in a time interval corresponds to the number of the particles detected in the time interval, providing a measure of analyte concentrations.

The foregoing discussion is illustrative and is not limiting. For example, some counters will not register a count until the falling edge of the comparator output is registered.

The pulse-counting mode of the first signal processor 164 offers good sensitivity, as it counts all voltage pulses that are resolved from each other and have a level that exceeds the reference level of the comparator 164'. The pulse-counting mode is effective as long as, e.g., the average time interval between consecutive voltage pulses is greater than the width of the voltage pulses, which allows the counter 164" to register each incoming pulse and reset before a next one comes.

A typical phenomenon associated with the pulse-counting mode is saturation of the comparator 164' at high input signal levels. As the rate at which amplifier 162" generates voltage pulses increases as a consequence of a larger number of particles scattering light onto optical detector 162, the average time interval between consecutive voltage pulses starts to become comparable to the width of the voltage pulses and the voltage pulses may start to overlap. If a pulse arrives at comparator 164' before the trailing edge of the preceding pulse has fallen below the reference level of the comparator 164' then counter 164" will only register one count instead of two, resulting in a detector response profile that no longer correlates directly with the quantity of the analytes.

Another problem associated with the pulse-counting mode occurs when a highly concentrated analyte elutes from chromatographic system 120 as a chromatographic peak. As the particles generated from this peak pass through the detector the incoming voltage pulses can overlap to such a degree that the comparator 164' output does not return to the level required to cause the counter 164" to reset, until the trailing edge of the chromatographic peak. Under these circumstances, the signal processor 164 simply loses outputting power, producing a distorted or saturated detector response profile for the analytes.

As shown in FIG. 4B, the second signal processor 166, running in an analog integration mode, includes a continuous integrator 166' and an analog-to-digital convertor 166". The continuous integrator 166' receives the voltage pulses generated from the optical detector 162 and may be a low pass filter designed so that it effectively averages the received voltages pulses over a time period that is long compared to the time width of a pulse but short compared to the time width of a chromatographic peak. The integrator output is sampled at regular intervals by the analog-to-digital converter 166" The resultant digital output is sent to the data station 168. The digitized data points collected in successive time intervals, as a chromatographic peak associated with one or more analytes passes through the system 100, are integrated to form a detector response profile for the analytes.

The analog integration mode, run by the second signal processor 166, resolves the issues associated with the pulse-counting mode, such as saturation or distortion of a detector response profile. Compared to the pulse-counting mode, the analog integration mode extends detection response linearity over a range of higher concentrations and thus accommodates a wider dynamic range. However, since the continuous integration mode does not possess the inherent ability of a comparator to discriminate against background noise, under non-saturating conditions, the output signal of the second signal processor 166 will always have a lower signal-to-noise ratio and reduced bandwidth relative to the output signal of the first signal processor 164 based on a comparator.

To exploit the benefits and avoid the disadvantages of the pulse-counting and analog integration modes, the optical detection system 160 incorporates both the pulse-counting first signal processor 164 and the analog integration based second processor 166. In some implementations, the voltage pulses produced from the optical detector 162 are sent simultaneously to both the processors 164 and 166, and the output signals from both the processors 164 and 166 are sent to the data station 168. The data station 168 decides which output to use based on a threshold criterion, which is associated with saturation of the first signal processor 164.

In some implementations, the threshold criterion can be established by calculating a slope of a line, which is constructed from two or more frequencies of the voltage pulses, outputted from the optical detector 162, measured at time points when the comparator 164' is to saturate. Alternatively, the threshold criterion can be decided by identifying a single frequency of the voltage pulses, above which the first signal processor 164 is known to saturate.

As discussed above, the data station 168 has a built-in intelligence, which, in some cases, monitors frequencies of the voltage pulses, as a chromatographic peak associated with one or more analytes passes through the system 100; compares the frequencies with a threshold criterion; and decides which output to use in formation of a detector response profile for the analytes, based on the threshold criterion. In some implementations, the data station 168 selects the output of the first signal processor 164 if the frequencies are below the threshold criterion and selects the output of the second signal processor 166 if the frequencies exceed the threshold criterion. By incorporating two processors 164 and 166 into the optical detection system 160 and selectively using one of the outputs at a time based on a threshold criterion, the optical detection system 160 extends response linearity over a range of high signal levels and preserves good sensitivity for weak signals.

The data station 168 can be commonly used computing systems. Examples of well known computing systems include, but are not limited to, embedded processors, personal computers, server computers, hand-held or laptop devices, multiprocessor systems, microprocessor-based systems, programmable consumer electronics, minicomputers, mainframe computers and the like known in the art.

Referring to FIG. 5, the particle-forming system 140, used by the system 100, includes a nebulizer 142, an evaporator 144 and a condenser 146.

A LC eluent or mobile phase carrying one or more separated analytes enters the nebulizer 142. The mobile phase can be a pure solvent or a mixture of more than one solvent and is more volatile than the analytes. In some implementations, the nebulizer 142, with an inert gas flowing through it, converts the LC eluent to a mist of droplets. The mist of droplets travels through the evaporator 144 and is heated by a desolvation gas, e.g., nitrogen. This may be the same inert gas flow used in nebulizer 142 or may comprise additional gas flow. The temperature of the evaporator 144 is controlled and regulated so that only the mobile phase evaporates, while the less volatile analyte droplets remain largely intact. The evaporation produces a stream of particles associated with the analytes.

Upon completion of the evaporation, the stream of the particles is directed to the condenser 146, which is filled with a supersaturated vapor, e.g., water or alcohol. Sometimes the particle stream may flow through a particle filter before passing into condenser 146. The use of such filters is known in the art and serves to reduce and the number of particles and to shape the particle size distribution. As the particles pass through condenser 146, each of them acts as a nucleation site, and the supersaturated vapor condenses onto the particles to grow the particles to sufficiently large sizes which will scatter light effectively. In some cases, through condensation nucleation, the particles, as small as a few nanometers, can grow to tens of micrometer in size.

The enlarged particles exit the condenser 146 by way of an orifice and travel through at least one incident light beam, which can be either a pulsed laser source that offers short and strong interaction with the particles, or a continuous-wave laser beam that provides steady interaction with the particles. The light strikes the particles and is scattered by the particles onto the optical detection system 160 of FIG. 1, and in other directions as well (not shown).

CNLSD, when used as a chromatographic detector, is often referred to as a universal detector, since its response is more independent of analyte nature than other commonly used detectors and can, in theory, detect any analytes that are less volatile than the mobile phase carrying the analytes. Other commonly used chromatographic detectors, e.g., ultraviolet light detectors, can only detect analytes that possess a chromophore; or, e.g., mass spectrometers, are limited to analytes that ionize; or, e.g., refractive index detectors, are sensitive to temperature and cannot usually be used when running a gradient.

Compared with other nebulizer based universal detection techniques, such as evaporative light scattering detection (ELSD), CNLSD utilizes a condensation step to grow the particles to a larger size prior to detection of the particles and is thus a more sensitive technique, as light scattering intensity is a function of particle size as measured by an optical sensor, such as a photodiode or PMT.

Figure 6:
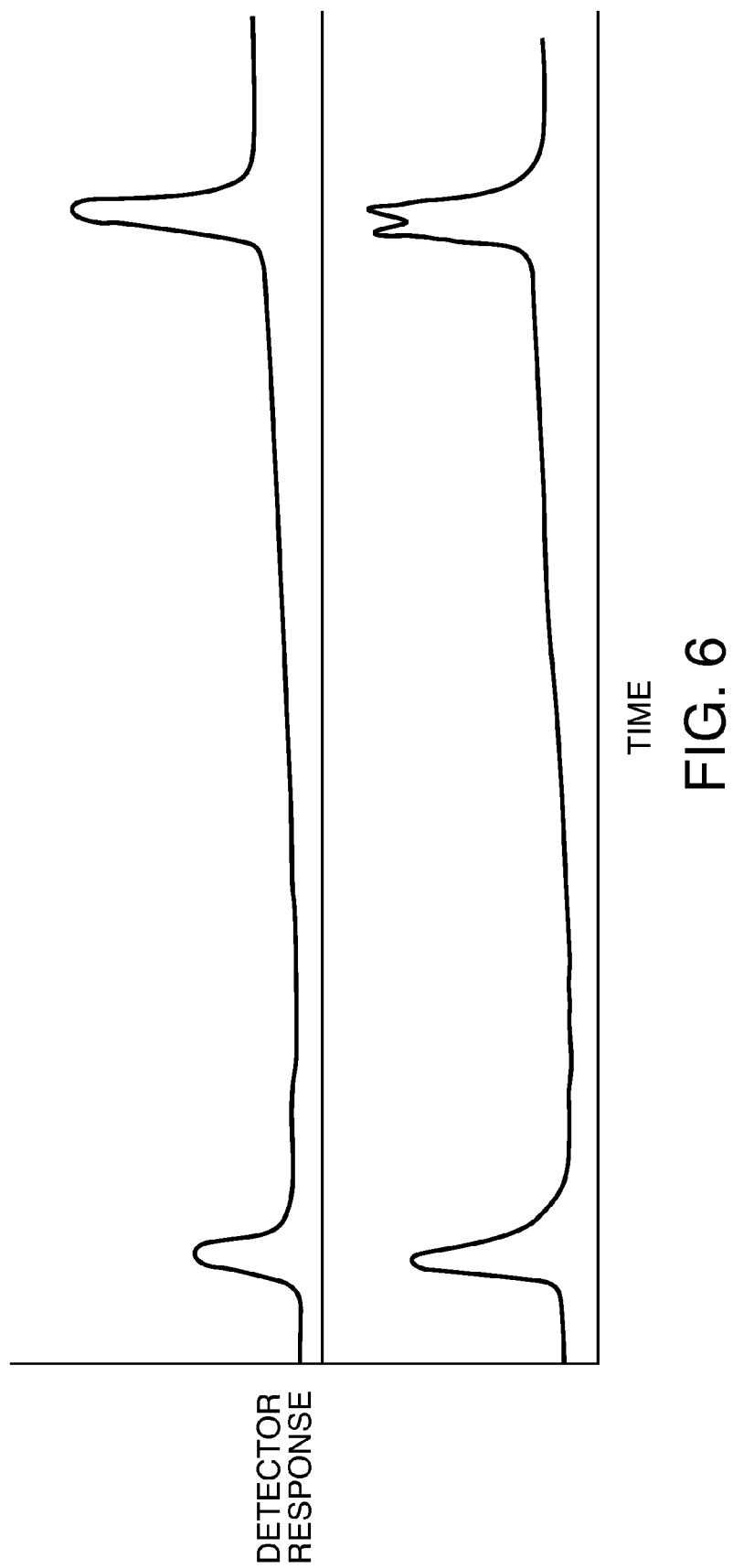
FIG. 6 is a graph of detection response versus time showing two curves, which illustrate the problem caused by high signal levels when using a single signal processor and a solution by complementary use of a second signal processor.

FIG. 6 is a graph of detection response versus time showing two curves, which illustrate the problem caused by high signal levels when using the first signal processor 164 alone and how the problem is solved by complementary use of the second signal processor 166.

As seen from FIG. 6, the lower trace shows a broadened or saturated peak caused by the comparator 164' of the first signal processor 164 being saturated when signal levels are high. The upper trace shows the identical scattered-light signal processed by the second signal processor 166, where the broadening effect or saturation of the peak is being avoided.

Although a number of implementations have been described in detail above, other modifications, variations and implementations are possible in light of the foregoing teaching.

For example, though, as described above, the amplified voltage signals are simultaneously fed to both processors 164 and 166, the voltage signals can only be directed to the processor 164 if analyte concentrations are low and to the processor 166 if analyte concentrations are high.

For example, though, as depicted in FIG. 3, the output signals from both the processors 164 and 166 are simultaneously sent to the data station 168 that decides which output to use based on a threshold criterion, the output from the first signal processor 164 can be a primary or first output to the data station 168, until a threshold criterion is met. At that point the primary output becomes the integrated signal from the second signal processor 166. When the signal falls from a high level, the process is reversed.

Variations, modifications, and other implementations of what is described herein will occur to those of ordinary skill in the art without departing from the scope of the invention as claimed. For example, some embodiments of an optical detection system include an integrated signal-processing and data-processing unit. Accordingly, the invention is to be defined not by the preceding illustrative description but instead by the scope of the following claims.

What is claimed is:

1. A chromatographic optical detection system comprising:
   an optical detector disposed to receive light scattered from a stream of particles and configured to convert the received light to an electrical signal;
   a signal-processing unit in signal communication with the optical detector to receive the electrical signal, and configured to convert the electrical signal to digital pulses and count the digital pulses to output a first signal corresponding to a number of particles detected in a time interval, and to integrate and digitize the electrical signal to output a second signal corresponding to the number of particles detected in the time interval; and
   a data station in signal communication with the signal-processing unit, and configured to select the first signal, if the number of particles detected in the time interval is less than a threshold criterion, and to select the second signal, if the number of particles detected in the time interval exceeds the threshold criterion, wherein the threshold criterion is associated with a saturation condition.

2. The system of claim 1, wherein the signal-processing unit comprises a first signal processor and a second signal processor, wherein the first signal processor is configured to convert the electrical signal to the digital pulses and count the digital pulses to output a first signal, the second signal processor is configured to integrate and digitize the electrical signal to output a second signal, and the saturation condition is associated with saturation of the first signal processor.

3. The system of claim 2, wherein the threshold criterion is a predetermined frequency of the amplified voltage pulses, above which the first signal processor is known to saturate.

4. The system of claim 3, wherein the data station selects the first signal if the frequencies of the amplified voltage pulses are below the threshold criterion and selects the second signal if the frequencies exceed the threshold criterion.

5. The system of claim 4, wherein the data station selects the first signal if the frequencies of the amplified voltage pulses are below the threshold criterion and selects the second signal if the frequencies exceed the threshold criterion.

6. The system of claim 1, wherein the optical detector comprises an optical sensor and an amplifier.

7. The system of claim 6, wherein the optical sensor comprises a photo-diode, a photo-diode array, or a photomultiplier tube.

8. The system of claim 2, wherein the first signal processor comprises a comparator and a digital counter.

9. The system of claim 2, wherein the second signal processor comprises a continuous integrator and an analog-to-digital convertor.

10. The system of claim 1, further comprising
a liquid chromatography system eluting a mobile phase carrying one or more analytes separated by the liquid chromatography system;
a nebulizer configured to spray the liquid chromatography eluent into a mist of droplets;
an evaporator configured to evaporate the mobile phase from the mist of droplets to produce a stream of particles associated with the one or more analytes;
a condenser comprising a supersaturated vapor, which condenses upon the particles to grow the particles to a larger size; and
at least one light source generating at least one beam of light that strikes the enlarged particles and is scattered by the enlarged particles;
wherein the light scattered by the enlarged particles is received by the optical detector and converted to the electrical signal.

11. The system of claim 10, wherein the mobile phase is a solvent or a mixture of more than one solvent.

12. The system of claim 10, wherein the analytes are less volatile than the mobile phase.

13. The system of claim 10, wherein the supersaturated vapor comprises water, an alcohol or any other suitable supersaturated solvent vapors.

14. The system of claim 13, wherein the alcohol is n-butanol.

15. The system of claim 10, wherein the larger size is in the range of about 100 nm to about 20 um.

* * * * *